(12) United States Patent
Hogan (10) Patent No.: US 7,035,686 B2
(45) Date of Patent: *Apr. 25, 2006

(54) COLOR-BASED NEUROFEEDBACK

(76) Inventor: Mark Bradford Hogan, 1742 Country Club Dr., Sugarland, TX (US) 77478

( * ) Notice: Subject to any disclaimer, the term of this patent is extended or adjusted under 35 U.S.C. 154(b) by 0 days.

This patent is subject to a terminal disclaimer.

(21) Appl. No.: 10/843,973

(22) Filed: May 12, 2004

(65) Prior Publication Data

US 2004/0210156 A1    Oct. 21, 2004

Related U.S. Application Data

(63) Continuation of application No. 10/078,129, filed on Feb. 19, 2002, now Pat. No. 6,795,724.

(51) Int. Cl.
*A61B 5/04* (2006.01)

(52) U.S. Cl. ........................................ 600/545

(58) Field of Classification Search ............... 600/544, 600/545; 128/920, 923
See application file for complete search history.

(56) References Cited

U.S. PATENT DOCUMENTS

| | | | |
|---|---|---|---|
| 4,263,561 A | 4/1981 | Weber | |
| 4,320,768 A | 3/1982 | Ledley et al. | |
| 4,474,186 A | 10/1984 | Ledley et al. | |
| 4,579,125 A * | 4/1986 | Strobl et al. | 600/544 |
| 4,747,082 A | 5/1988 | Minato et al. | |
| 4,919,143 A | 4/1990 | Ayers | |
| 4,928,704 A | 5/1990 | Hardt | |
| 4,949,726 A | 8/1990 | Hartzell et al. | |
| 4,955,388 A | 9/1990 | Silberstein | |
| 5,003,300 A * | 3/1991 | Wells | 345/8 |
| 5,010,891 A | 4/1991 | Chamoun | |
| 5,020,538 A | 6/1991 | Morgan et al. | |
| 5,024,235 A | 6/1991 | Ayers | |
| 5,123,899 A | 6/1992 | Gall | |
| 5,135,468 A | 8/1992 | Meissner | |
| 5,211,178 A | 5/1993 | Kado et al. | |
| 5,213,562 A | 5/1993 | Monroe | |
| 5,220,921 A | 6/1993 | Ferris et al. | |
| 5,224,864 A | 7/1993 | Vavagiakis | |
| 5,230,344 A | 7/1993 | Ozdamar et al. | |
| 5,241,967 A | 9/1993 | Yasushi et al. | |

(Continued)

OTHER PUBLICATIONS

"New helmet getting attention of those with ADHD"; Jeffrey Bair, Houston Business Journal, Nov. 23-29, 2001, pp. 21, 23.

(Continued)

*Primary Examiner*—Eric F. Winakur
(74) *Attorney, Agent, or Firm*—Conley Rose, P.C.

(57) ABSTRACT

A neurofeedback technique uses color as its feedback cue. A preferred embodiment of the invention includes an amplifier that receives EEG signals from electrodes (e.g., adhesive electrodes, SQUID sensors, etc.) on or adjacent the person's scalp, a low or band pass filter, a color processor and a display. The color processor converts an aspect of one or more channels of the person's EEG signal(s) to a color and shows that color to the person on the display. The aspect of the EEG that is converted to color can be the frequency or the amplitude of the person's EEG signal(s). If EEG amplitude is used in the conversion process, the instantaneous, average or peak amplitude can be used. This process is dynamic, meaning that the system repeatedly converts the EEG signal to color. Conventional adhesive electrodes or non-adhesive sensors can be used to detect the person's brain activity.

11 Claims, 3 Drawing Sheets

U.S. PATENT DOCUMENTS

| | | | |
|---|---|---|---|
| 5,267,942 | A | 12/1993 | Saperston |
| 5,289,438 | A | 2/1994 | Gall |
| 5,295,491 | A | 3/1994 | Gevins |
| 5,306,228 | A | 4/1994 | Rubins |
| 5,320,109 | A | 6/1994 | Chamoun et al. |
| 5,325,872 | A | 7/1994 | Westermann |
| 5,331,969 | A | 7/1994 | Silberstein |
| 5,352,181 | A | 10/1994 | Davis |
| 5,356,368 | A | 10/1994 | Monroe |
| 5,363,858 | A | 11/1994 | Farwell |
| 5,365,939 | A | 11/1994 | Ochs |
| 5,374,193 | A | 12/1994 | Trachtman |
| 5,377,258 | A | 12/1994 | Bro |
| 5,406,957 | A | 4/1995 | Tansey |
| 5,409,445 | A | 4/1995 | Rubins |
| 5,447,166 | A | 9/1995 | Gevins |
| 5,450,855 | A | 9/1995 | Rosenfeld |
| 5,458,117 | A | 10/1995 | Chamoun et al. |
| 5,465,729 | A | 11/1995 | Bittman et al. |
| 5,467,777 | A | 11/1995 | Farwell |
| 5,571,057 | A | 11/1996 | Ayers |
| 5,709,645 | A | 1/1998 | Siever |
| 5,877,447 | A | 3/1999 | Vice |
| 5,899,867 | A | 5/1999 | Collura |
| 6,195,576 | B1 | 2/2001 | John |
| 6,269,262 | B1 | 7/2001 | Kandori et al. |
| 6,275,719 | B1 | 8/2001 | Kandori et al. |
| 6,291,759 | B1 | 9/2001 | Turner |
| 2003/0109797 | A1* | 6/2003 | Kim et al. ............... 600/545 |

OTHER PUBLICATIONS

"Biopotential Amplifiers", Michael R. Neuman, Chapter 6, Medical Instrumentation Application and Design, Second Edition, 1992, pp. 288-349.

* cited by examiner

COLOR-BASED NEUROFEEDBACK

CROSS-REFERENCE TO RELATED APPLICATIONS

This application is a continuation of and claims priority to U.S. patent application Ser. No. 10/078,129 now U.S. Pat. No. 6,795,724, entitled "Color-Based Neurofeedback", filed on Feb. 19, 2002 and included herein by reference.

STATEMENT REGARDING FEDERALLY SPONSORED RESEARCH OR DEVELOPMENT

Not applicable.

BACKGROUND OF THE INVENTION

1. Field of the Invention

The present invention generally relates to neurofeedback equipment and techniques. More particularly, the invention relates to the use of color in a neurofeedback system.

2. Background Information

For many years, neurologists, psychotherapists, researchers, and other health care professionals have studied the human brain. One commonly studied parameter is the electrical activity of the brain. Using electrodes adhered to a person's scalp in conjunction with associated electronics (amplifiers, filters, etc.), an electroencephalogram ("EEG") is recorded over a given time period depicting the electrical activity of the brain at the various electrode sites. In general, EEG signals (colloquially referred to as "brain waves") have been studied in an effort to determine relationships between frequencies of electrical activity or neural discharge patterns of the brain and corresponding mental, emotional and cognitive states. As a result of this type of work, it has become generally accepted that monitoring a person's EEG and providing feedback information to the person as a function of the EEG can actually serve to enable a person to voluntarily reach or maintain a target mental state and enhance performance in certain areas. This type of feedback technique is referred to generally as "neurofeedback."

As a function of time, EEG signals appear to the untrained eye as seemingly random squiggles on a paper chart or display. Upon more careful inspection, the EEG signals typically follow a pattern of sorts, with peaks and valleys crudely approximating a sinusoidal waveform. The number of peaks of an EEG per second is referred to as the "frequency" and is measured in units of Hertz ("Hz"). The frequency of EEG signals vary from site to site on the head, and also vary as a function of the mental state of the person.

A standard has been used for many years to permit easy reference to EEG frequencies. Table I below shows eight standardized frequency bands and the typical mental state associated with each band.

TABLE I

EEG Designations

| Name | Frequency range (Hz) | General Subjective State |
| --- | --- | --- |
| Delta | 0–4 | Sleep, unconscious processing |
| Theta | 4–7 or 4–8 | Deeply relaxed, inwardly focused |
| Alpha | 8–12 or 8–13 | Very relaxed, passive attention |
| Beta | >13 | External attention |
| SMR Beta | 12–15 | Relaxed, external attention |

TABLE I-continued

EEG Designations

| Name | Frequency range (Hz) | General Subjective State |
| --- | --- | --- |
| Mid Beta | 15–18 | Active, external attention |
| High Beta | 18–35 | Anxiety, external attention |
| Gamma | >30 or >35 | Peak performance states or a consolidation frequency |

More recently, practitioners have referred less often to the frequency bands by their Greek labels and more often to numerical range of the band (e.g., the "1–3 Hz" band). This is largely a result of many practitioners delineating the frequency bands differently.

Numerous neurofeedback techniques have been attempted over the years. Common to many of these techniques is the use of discrete visual or audible feedback signals or cues that relate in some predetermined manner to the person's EEG signals. These techniques typically compare the frequency of an EEG signal to a predetermined frequency threshold or frequency range and provide one visual feedback signal if the EEG frequency is within the range and a different feedback signal if the frequency is outside the range. The person being trained uses these feedback signals to modify the electrical activity of one or more areas of the brain thereby achieving a target mental state. Examples of such techniques are described in U.S. Pat. Nos. 5,024,235 and 5,899,867.

Although satisfactory to some degree in certain applications, such techniques are generally self-limiting in their ability to display the full range of frequencies at a wide variety of cortical sites in an intuitively easy to understand format. For example, in FIGS. 14–18 of U.S. Pat. No. 5,899,867 (U.S. Pat. No. 5,899,867 incorporated herein by reference in its entirety), a simplistic facial image is shown as the feedback image to the person. The face has two eyes, two eyebrows, a nose and a mouth. The mouth is controlled by the amplitude of the alpha waves (8–12 Hz), and the eyebrows are controlled by the theta wave (4–7 Hz) amplitude. As a form of neurofeedback therapy, this type of visual representation can be difficult for a patient to reconcile and process in a useful manner. Moreover, conventional feedback techniques typically require more of a conscious effort to focus on the task at hand and learn the format for very narrow control.

Additionally, conventional electrodes that are adhered to a person's scalp for neurofeedback therapy typically use a sticky conductive paste that is messy to apply and messy to clean up afterwards. Further, the time required to correctly position the electrodes and verify that a sufficiently low impedance exists between each electrode and the scalp is relatively long, and the process is generally inconvenient to the person being monitored.

Accordingly, an improved neurofeedback technique is needed, particularly one that avoids or minimizes the feedback issues noted above and the mess and inconvenience involved with adhesive-type electrodes.

BRIEF SUMMARY OF THE PREFERRED EMBODIMENTS OF THE INVENTION

The problems noted above are solved in large part by a neurofeedback technique and apparatus that uses color as its feedback cue, and preferably that employ non-adhesive sensors. A preferred embodiment of the invention includes an amplifier that receives EEG or magnetoencephalogram ("MEG") signals from electrodes on or adjacent to the person's scalp, a low or band pass filter, a color processor and a display unit. The color processor converts an aspect of one or more channels of the person's EEG signal(s) to a color and shows that color to the person on the display. The aspect of the EEG that is converted to color can be the frequency or the amplitude of the person's EEG signal(s). If EEG amplitude is used in the conversion process, the instantaneous, average or peak amplitude can be used. This process is dynamic, meaning that the system repeatedly converts the EEG signal to color while the person is receiving neurofeedback training.

By using color as the feedback signal, a plurality (theoretically, an infinite number) of feedback signals can be provided to the user during a feedback session. This is in contrast to many conventional feedback systems which simply inform the person whether, or not, the frequency of the EEG is within a single predetermined frequency range. Also, color-based neurofeedback signal is generally much easier to understand and follow than many types of feedback images heretofore known.

In addition to, or instead of, color, audio can be used as a feedback signal. For example, one audio tone can be generated to inhibit a person's neuro response and another tone can be used to reward a different response.

The display unit used to provide the color-based feedback information to the user can be a single, stand-alone display (e.g., computer display). Alternatively, the display unit may comprise a pair of displays, one for each eye, such as in the form of head worn goggles. With a pair of displays, the color processor can provide the same or different images and colors to each eye of the person being trained. This provides considerable flexibility in the type of neurofeedback training scenarios the person being trained or a health care professional might desire.

The neurofeedback system described herein may use conventional electrodes that adhere to a person's scalp with conductive paste. Alternatively, however, the system may use EEG sensors that do not require conductive paste. This latter type of sensor generally detects the electromagnetic energy emanating from a point or area associated with a person's brain and does not directly contact the person's scalp, at least not to the same extent as is generally required for conventional adhesive electrodes. One suitable type of non-adhesive sensor is the Superconducting Quantum Interference Device ("SQUID").

The system described herein advantageously uses color as its feedback information to provide an enhanced neurofeedback experience. Many aspects of the system are fully programmable, such as specifying the EEG channels to be monitored, the colors to be used, whether frequency or amplitude is to be converted to color, etc. Further, the system may use conventional electrodes (which use conductive paste to adhere the electrode to a person's scalp) or non-adhesive sensors which avoid the use of the paste and minimize the mess and time involved with adhesive electrodes. These and other advantages and benefits will become apparent upon reviewing the following disclosure.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. As one skilled in the art will appreciate, companies and individuals may refer to components and sub-components by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either a direct or indirect electrical connection. Thus, if a first device couples to a second device, that connection may be through a direct electrical connection, or through an indirect electrical connection via other devices and connections. Further, the term "EEG" is understood to refer to electroencephalogram or magnetoencephalogram signals. Also, the term "neurofeedback" generally refers to any technique wherein a person is provided with a sensory cue (e.g., visual, audible) which dynamically varies as a result of changing EEG signals. To the extent that any term is not specially defined in this specification, the intent is that the term is to be given its plain and ordinary meaning as understood by a person of ordinary skill in the art.

DETAILED DESCRIPTION OF THE PREFERRED EMBODIMENTS

By way of a high level overview, the preferred embodiments of the present invention use color in a neurofeedback system. The user's EEG is monitored and converted into color patterns that are shown to the user via a display. In response, the user's brain, modifies its electrical activity to cause a change in the color to a desired level (e.g., color, hue, etc.).

Figure 1:
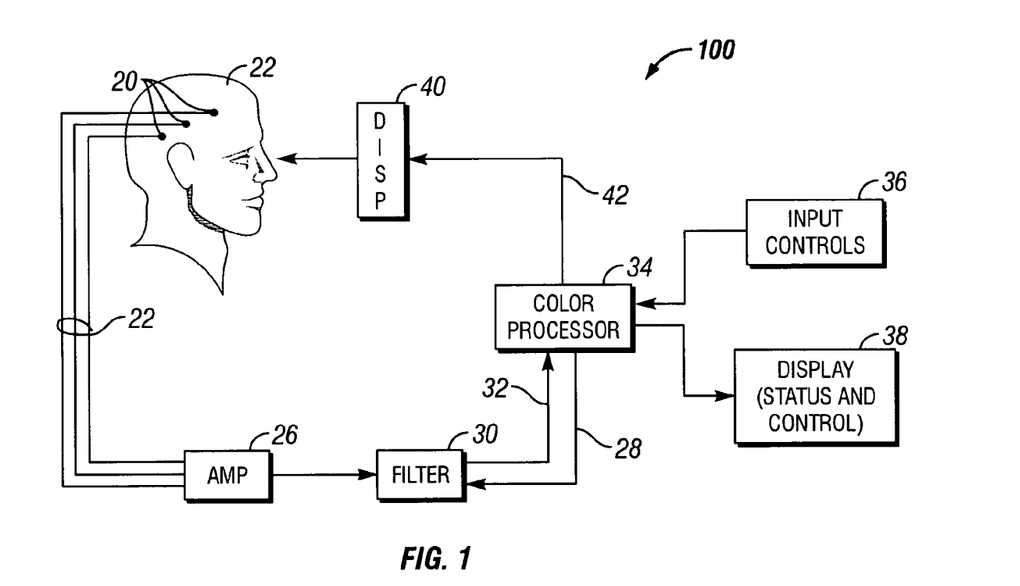
FIG. 1 shows a preferred embodiment of the present invention including a neurofeedback system in which color is used as the feedback signal.

Referring now to FIG. 1, in accordance with a preferred embodiment of the invention, neurofeedback system 100 includes one or more electrodes 20 coupled to an amplifier 26, a filter 30, a color processor 34 and a display 40. In general, the electrodes 20 detect electrical signals or electromagnetic waves through the person's scalp 22 and provides those signals via conductors 22 to the amplifier 26.

Although three electrodes are shown in FIG. 1, it should be understood that any number of electrodes can be used. Also, the electrodes depicted in FIG. 1 are shown as being conventional electrodes that use conductive paste to be closely adhered to the person's scalp. Alternatively, sensors that do not use conductive paste can be used. These types of electrodes are discussed below.

Referring still to FIG. 1, the amplifier 26 comprises an amplifier that increases the amplitude of the EEG signals received by electrodes 20. The amplified signals are then processed by filter 30 which preferably comprises a low pass or band pass filter. Although shown as separate units, amplifier 26 and filter 30 may be assembled as a single unit. Amplifier 26 and filter 30 are well known in the art and, accordingly, are not described in further detail. More information regarding suitable implementations of amplifier 26 and filter 30 can be found in U.S. Pat. No. 4,263,561 and Chapter 6 (pages 288–348) of *Medical Instrumentation Application and Design,* 2nd ed., 1992, both of which are incorporated herein by reference. The amplified and filtered output signal 32 from filter 30 is provided to color processor 34 which will be described below. It is generally recognized that the frequency of EEG signals fall within the range of 0 to 50 Hz and thus, the filter 30 may be set to attenuate all frequencies greater than 50 Hz. Additionally, as explained below, it may be desirable to examine an EEG channel for a particular frequency or range of frequencies. The filter 30 can be programmed to filter for such a particular frequency or frequency range. In accordance with one embodiment of the invention, the color processor 34 provides a control signal 28 to the filter 30 that the filter employs to set its frequency response to a desired level.

Referring still to FIG. 1, color processor 34 couples to input controls 36 and an output device 38, which preferably comprises a display. The color processor 34 may be controlled via input controls 36 and provide information (e.g., status and control information) on display 38. Using the input controls 36 and display 38, a user can operate and program the color processor 34. The color processor 34 may be a computer and the input controls 36 may comprise a keyboard, mouse, etc. In that context, the display 38 would comprise the computer's display. Alternatively, the color processor 34 may comprise discrete logic designed for the purposes stated herein.

In addition to color, an audio signal can be provided to the person via speakers or head phones (not shown). Audio can be used as a feedback signal. For example, one audio tone can be generated by processor 34 (or other logic) to inhibit a certain neuro response and another tone can be used to reward a different response.

In accordance with the preferred embodiment of the invention, the color processor 34 converts the amplified and filtered EEG signals from filter 30 to one or more colors for displaying to the person being trained on display 40. The output signal 42 from color processor 42 preferably comprises a signal that provides or otherwise indicates the color(s) to be shown on the display 40. The output signal 42 may comprise a standard NTSC-based signal, VGA signal or other types of signal in accordance with any other suitable format. The output signal could simply be a digital color value that is converted by the display 40 into a suitable video signal.

Figure 7:
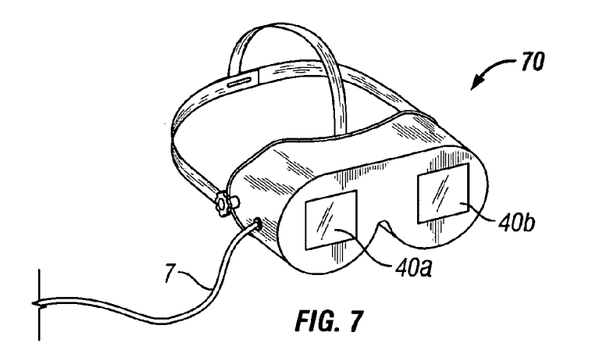
FIG. 7 shows a head worn display unit in the form of goggles having two separate displays.

The display 40 may comprise a stand alone, single display, such as a cathode ray tube ("CRT"), a liquid crystal display ("LCD"), an organic liquid crystal display ("OLCD") and the like. Alternatively, as shown in FIG. 7, the display unit 40 may comprise head worn goggles 70 in which a separate display 40a, 40b is provided for each eye. The CyberEye™ series of goggles (e.g., the CE-200 head mounted display) provided by the Ireality.com, Inc. are suitable examples of such goggles.

Using system 100, the electrical activity of the person's brain is detected and processed and color images are provided in a feedback loop to the person. The visible part of the electromagnetic spectrum is generally recognized as including the colors from red having a wavelength of approximately 700 nanometers, to violet at approximately 400 nanometers. In accordance with the preferred embodiment, color is used as the feedback visual cue. Color is advantageous over many types of conventional feedback cues, in which one or two images are presented to the user based on whether a brain wave is within or outside of a particular frequency range. Using color there are numerous, if not infinite, variations for the visual presentation to the person. This point is illustrated with reference to FIG. 2.

Figure 2:
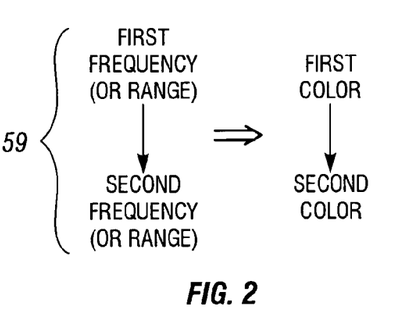
FIG. 2 illustrates conceptually the conversion of EEG frequency to a color value.

Referring to FIG. 2, the color processor 34 converts an EEG frequency (detected by electrodes 20) to a color value that is dependent upon the frequency detected. Thus, a range of frequencies 59 from a first frequency to a second frequency, can be converted to a range of color values from a first color value to a second color value. All of the unique colors and shades of color between the first and second colors correspond to the frequencies between the first and second frequencies. For example, the first and second frequencies might be 4 Hz and 35 Hz, respectively. The first and second colors might be red and blue, respectively. If the frequency resolution of the system is 1 Hz, there would be 30 frequency increments between 4 and 35 Hz (i.e., 5 Hz, 6 Hz, 7 Hz, . . . 34 Hz) in frequency range 59. Accordingly, the color range would include 30 different colors between red and blue (e.g., yellow, orange, green, various shades of red, yellow, orange, etc.).

The frequencies comprising the range of frequencies 59 in FIG. 2 may be individual frequencies, as explained above, or ranges of frequencies. In this latter case, each element of frequency range 59 is itself a range of frequencies. For example, the first frequency may be 1–3 Hz, the next element 4–6 Hz, etc. The color processor 34 selects the color that corresponds to the frequency, or frequency range, that most closely matches the person's EEG frequency.

Figure 3:
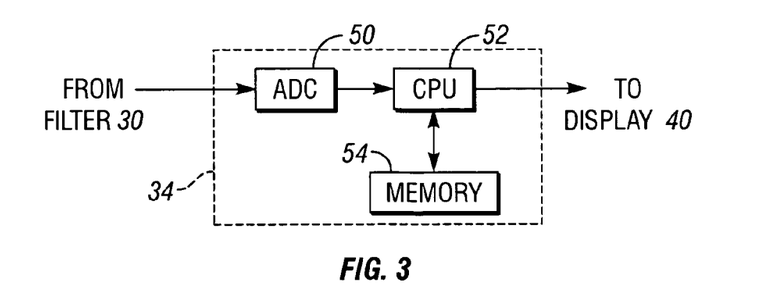
FIG. 3 shows one embodiment of how EEG frequency can be converted to color.
Figure 4:
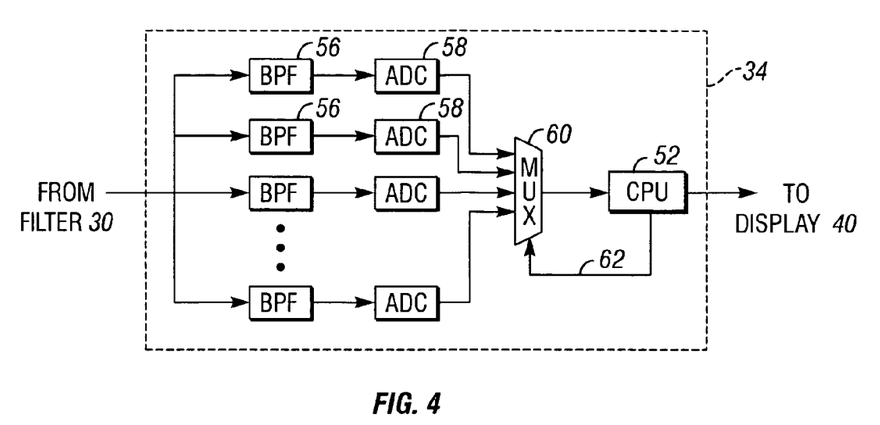
FIG. 4 shows an alternative embodiment of how EEG frequency can be converted to color.

The color processor 34 preferably performs the function of converting EEG frequency to color, although this function may be performed by the amplifier 26 or filter 30. FIGS. 3 and 4 show two exemplary embodiments of the color processor 34 to perform the frequency-to-color conversion function. One of ordinary skill in the art should recognize that the color processor 34 will include other components as well, such as components necessary for driving the display 40. In FIG. 3, color processor 34 preferably includes an analog-to-digital converter ("ADC") 50 coupled to a central processing unit ("CPU") 52 which couples to memory 54. Memory 54 may comprise non-volatile memory (e.g., read only memory, hard disk drive, etc.) and/or volatile memory (e.g., random access memory). As such, memory 54 may be used for storage of the software executed by CPU 52 to perform the functionality described herein, as well as to provide temporary storage for data during operation.

Referring still to FIG. 3, the amplified and filtered analog output signal 32 from the filter 30 (FIG. 1) is converted from an analog form to a digital form by ADC 50. Analog-to-digital converters are well known in the electronics art. Once in digital form, the filter 30 output signal is provided to CPU 52, which may be any suitable programmable, general purpose microcontroller. One of the functions performed by the CPU 52 is to convert the digitized time-domain filter 30 output signal to the frequency domain. Any of a variety of well-known techniques can be used in this regard. For example, the CPU 52 can perform a "discrete Fourier transform" of the signal from ADC 50. As one of ordinary skill in the art would know, the discrete Fourier transform produces a set of values that corresponds to the frequency content of the signal. Alternatively, CPU 52 can be programmed to perform the well-known "Fast Fourier Transform." Regardless of which type of time-to-frequency conversion technique is implemented, the CPU 52 determines or approximates the frequency spectrum of the filter's output signal, and thus the frequency spectrum of the EEG signal.

The EEG waveforms are the summated synaptic potentials generated by the pyramidal cells of the cerebral cortex. The frequencies and amplitudes are determined by special arrangement of excitatory and inhibitory interconnections among cells. With billions of neurons and thousands of synaptic connections per neuron, the EEG waveform is not a pure sinusoid, its frequency content can include a predominant frequency component and various other frequency components. The amplitude of the predominant frequency component will be larger than those of the other frequency components. The CPU 52 preferably is programmed to determine the largest frequency component and recognize that component as the predominant frequency component. The CPU then compares the frequency of the predominant frequency component to predetermined or programmed ranges of frequencies corresponding to the various ranges depicted in FIG. 2. Once the CPU 52 determines the frequency range to which the predominant frequency component corresponds, the CPU 52 then selects the predetermined color corresponding to that frequency range for display on display 40.

An alternative embodiment of the frequency-to-color conversion capability of the color processor 34 is shown in FIG. 4. The embodiment of FIG. 4 includes a plurality of band pass filters 56, each coupled to an ADC 58. The digital output signals from the ADCs 58 are time multiplexed by multiplexer 60 which is controlled via control signal 62 generated by CPU 52. The multiplexer 60 provides one of the digital signals from ADCs 58 as its output signal to the CPU based on the status of the control signal 62. Accordingly, the CPU 52 can individually select a digital signal from the ADCs 58 for further processing.

Each band pass filter 56 preferably corresponds to a frequency or frequency range of interest as in FIG. 2. Rather than performing a Fourier transform as in FIG. 3, the plurality of band pass filters 56 is used to determine in which frequency range the predominant frequency of the EEG signal corresponds. Each band pass filter 56 has an upper frequency cutoff and a lower frequency cutoff and passes any frequencies that fall within the frequency range between the upper and lower cutoffs. All other frequencies are attenuated. Each band pass filter 56 thus has a band pass frequency range that corresponds to the plurality of frequencies or frequency ranges as in FIG. 2. The predominant frequency component of the EEG signal can be ascertained by determining which band pass filter has the largest magnitude output signal. The frequency range corresponding to that band pass filter corresponds to the EEG predominant frequency component. The CPU 52 can make that determination by using the control signal 62 to sequence through the digital output signals from the ADCs 58 and determine which ADC provides the highest amplitude signal. The CPU 52 preferably sequences through the ADC output signals to determine the largest amplitude signal at a sufficiently fast rate given typical EEG frequencies. For example, the CPU may sequence all ADCs at a rate of one loop every 1 microsecond. Once the CPU 52 determines the predominant frequency of the EEG, as before, it selects the color corresponding to that frequency range to display on display 40.

Figure 5:
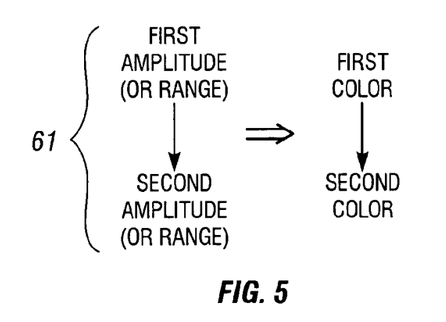
FIG. 5 illustrates conceptually the conversion of EEG amplitude to a color value.

Rather than converting EEG frequency to color as in FIG. 2, alternatively, EEG amplitude can be converted to color. As shown in FIG. 5, a range of amplitudes 61, from a first amplitude to a second amplitude, can be converted to a range of color values from a first color value to a second color value. As before, each amplitude element of the range 61 may itself be an amplitude range. The EEG amplitudes preferably represent the average amplitude of the EEG signal as explained below. All of the unique colors and shades of color between the first and second colors correspond to the amplitudes between the first and second amplitude. For example, the first and second amplitudes might be 5 mv and 15 mv, respectively. The first and second colors might be red and blue, respectively. If the amplitude resolution of the system is 1 mv, there would be 10 mv worth of amplitudes (i.e., 5 mv, 6 mv, 7 mv, etc.) between 5 and 15 mv. Accordingly, the color range would include 10 different colors between red and blue (e.g., yellow, orange, green, various shades of red, yellow, orange, etc.).

In the embodiment using EEG amplitude, any measure or computation of signal amplitude can be used. For example, instantaneous amplitude can be used to convert to a color. FIG. 3 shows a block diagram suitable for this embodiment. The EEG signal output from the filter 30 is digitized by an A/D converter 50 and CPU 52 simply compares each digitized point to a color value by comparing the amplitude of the digitized point to a plurality of amplitude ranges as in FIG. 5.

Figure 6:
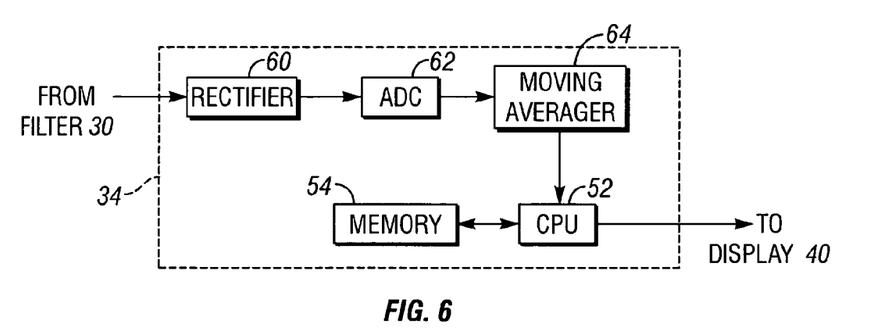
FIG. 6 shows one embodiment of how EEG amplitude can be converted to color.

Alternatively, average signal amplitude can be used in the color conversion process. Any one of a variety of techniques can be used to determine the average amplitude of the EEG signal. An example is shown in FIG. 6 in which the color processor 34 includes a rectifier 60, an ADC 62, a moving averager 64, a CPU 52 and memory 54. The rectifier 60 (optional) ensures that the signal being processed is only of positive voltage. The rectifier 60 signal is then digitized by the ADC 62. The moving averager 64 receives the digitized version of the rectified signal and computes an average of the last n number of samples of the rectified and digitized EEG waveform. The value n can be any suitable predetermined or programmable value. For example, n may be a number of samples that corresponds to the last five seconds of the EEG signal. The CPU 52 receives the average value from the moving averager 64 and converts that average amplitude value to a color value.

Instead of instantaneous or average amplitude, peak amplitude can alternatively be used to convert to a color. In this case, the color processor 34 would have a peak detection circuit (not specifically shown), which are well known, or the CPU 52 as in FIG. 3 could be programmed to analyze the incoming digitized EEG waveform for peak values. The peak value could then be compared to a range of peak amplitude values and converted to a predetermined corresponding color.

As noted above, the display unit 40 may comprise a stand-alone display or a head worn display unit in the form of goggles. If the display is implemented as a stand-alone display, the user, of course, will view a single display of varying color in relation to an aspect (e.g., frequency, amplitude) of the EEG waveform. In the form of goggles, the display unit 40 may comprise two miniature displays, one for each eye, as represented by goggles 70 in FIG. 7.

As shown in FIG. 7, the goggles 70 include a display 40a for the left eye and a separate display 40b for the right eye. As noted above, each display can be separately controlled. This feature permits the color processor 34 to drive each display 40a, 40b with the same or different image and the same or different colors. With different colors presented to each eye, the user could be instructed to strive for making the two displays show the same color. Also, one display/eye could be exposed to a predetermined color and the other display could show a color that, as explained above, is a function of the frequency or amplitude of the EEG signal. Further still, on each display 40a, 40b a plurality of color fields can be shown relative to the person's EEG. Thus, two or more different color fields can be shown independently to each eye and each eye can be presented with two or more colors that differ, in at least one color, with the colors presented to the other eye.

Figure 8:
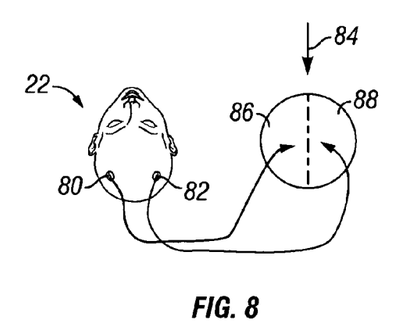
FIG. 8 shows one embodiment of how electrode location can be correlated to a color image on a display.

As noted above, one or more electrodes on the person's scalp can be used to implement the color-based neurofeedback technique described herein. The EEG signal from each electrode is referred to as a "channel." Numerous variations of using multiple EEG channels are possible. For example, in FIG. 8, two electrodes 80 and 82 are placed on the person's scalp 22. Two color portions 86 and 88 of an image 84 are shown on a display 40 for each electrode signal. Thus, the EEG signal from electrode 80 can be used to drive the color portion 86 and, similarly, the EEG signal from electrode 82 can be used to drive the color portion 88. The two color portions 86 and 88 can be shown on a stand-alone display or on separate displays as explained above.

Figure 9:
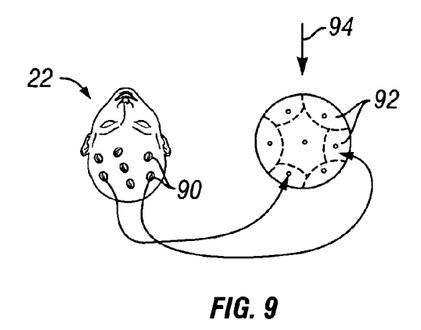
FIG. 9 shows an alternative embodiment of how electrode location can be correlated to a color image on a display.

In FIG. 9, more than two electrode channels 90 (specifically 7 in the example of FIG. 9) correspond to a like number of color portions 92 (i.e., 7) in an image 94 on a display 40. The orientation of the color portions 92 on the displayed image 94 can approximate the orientation of the electrode placement as shown or be in any other desired orientation. It should be understood that any number of electrodes can be implemented. For example, if the industry standard "10–20" system is used, there will be 19 electrodes and 19 color portions on the display 40.

Apart from converting an EEG channel (frequency or amplitude) to a color, the color processor 34 could convert the difference between two electrode channels to a color. As such, the color processor 34 could compute the difference in frequency or amplitude between two electrode channels. The computed difference could then be compared to a plurality of ranges and the color associated with the corresponding range could be selected to show on display 40.

The neurofeedback system 100 described herein preferably is fully programmable. Numerous aspects of the operation of the system can be programmed by an operator. Such aspects include, but are not limited to:
the colors available to be shown on display unit 40
whether frequency or amplitude is monitored for conversion to color
the range of frequencies to monitor
the mapping between frequencies and colors (FIG. 2)
the range of amplitudes to monitor
the mapping between amplitudes and colors (FIG. 5)

As noted above, the system described herein may use sensors to detect brain wave activity that do not require the use of conductive paste. One suitable type of such a sensor is the Superconducting Quantum Interference Device ("SQUID"). In general, a SQUID sensor operates at a cryogenic temperature at which metal loses its electrical resistivity. In one type of SQUID, a metal film is deposited on a quartz cylinder having a narrow bridge "weak link." A magnetic field will increase the energy, making the superconducting state unstable so that the weak link converts to its normal state (non-superconducting), thereby allowing one flux quantum to enter. The conduction of the ring is monitored by a radio frequency circuit whose sensitivity is increased with a feedback current circuit. Generally a "flux transporter" is used in which a primary coil ("detection coil"), of superconductive wire, is connected to a secondary coil ("input coil") contained in the superconducting chamber with the SQUID. For example, the chamber may comprise "dewar" vacuum chamber filled with liquid helium or nitrogen. For example, a plurality of primary coils are placed closely about the patient's head to detect the brain's magnetic fluxes. Those fluxes create responses in the detection coils which are communicated to the SQUIDs. In response, the SQUIDs produce a voltage proportional to the net magnetic flux on each detection coil.

Figure 10:
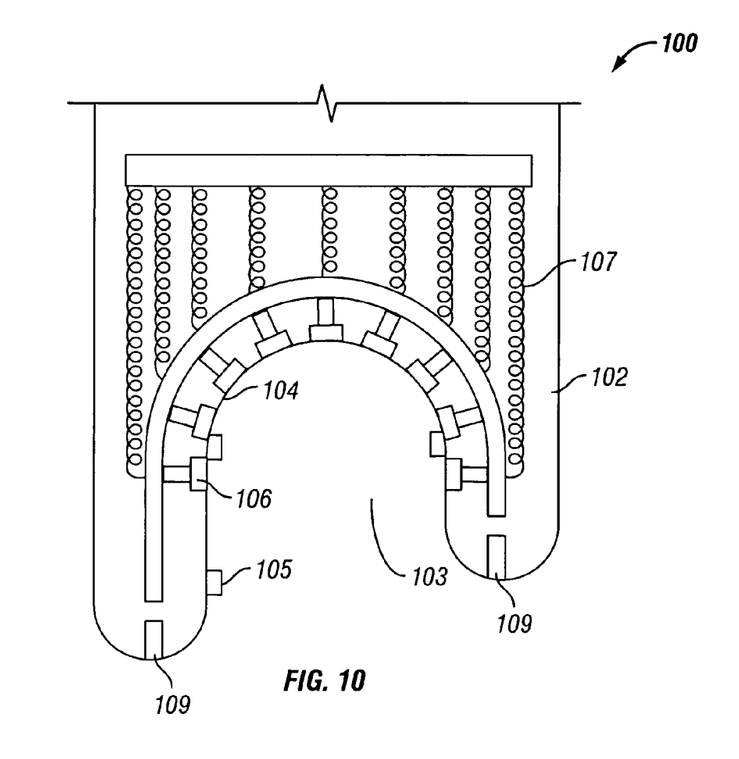
FIG. 10 shows an exemplary embodiment of the use of non-adhesive SQUID sensors in place of conventional adhesive electrodes.

An exemplary configuration of the use of SQUID sensors is shown in FIG. 10. The configuration includes a dewar vacuum chamber 100 having a dewar tail end 102 with a helmet-shaped cavity 103 and fiducial marks 109. The wall 104 facing the subject's head has inflatable thin bladders (cuffs) 105 positioned between the sensors 106. The sensors 106 (9 shown) are mounted in an array on a support shell (not specifically shown). The sensors 106 are connected by wires 107 to electronics contained elsewhere (e.g., color processor 34) which receive signals from the sensors 106 and process the signals in accordance with known SQUID-based techniques. Each sensor 106 preferably comprises a detector coil (flux transformer) and a SQUID. All of the components within the dewar preferably are covered by liquid helium or nitrogen at a cryogenic temperature. Explanations of SQUID sensors and their use can be found in U.S. Pat. Nos. 6,275,719, 6,269,262, 6,195,576, 5,211,178, and 5,020,538, all of which are incorporated herein by reference.

SQUID-based sensor systems typically are employed in a magnetically shielded room to prevent externally generated magnetic noise from interfering with the minute magnetic fields emanating from a person's brain. Even the magnetic fields from a car passing outside the building in which a SQUID system is housed can interfere with the signals being monitored. The shielded room preferably comprises aluminum and mu-metal layers. Mu-metal is a high permeability magnetic shielding material typically made of non-oriented 80% nickel-iron-molybdenum alloy annealed at approximately 1900° F. If such shielding is undesirable, any technique for eliminating the effects of magnetic noise is acceptable. One such suitable technique is described in U.S. Pat. No. 5,020,538, incorporated herein by reference.

Further, if noise from a display or goggles is a concern for the SQUID sensors, a SQUID sensor can be placed near the goggles to sense its signals and use that signal to cancel out the noise detected by other SQUID sensors. Alternatively, the display can be placed outside the room in which the person is using equipment. In this embodiment, the images from the display can be provided to the person via one or more mirrors through a light pipe such as a periscope configuration.

The system described herein can be used therapeutically in many ways. As an example, if the practitioner wanted to treat a behavior symptom such as depression which was believed to result from left brain under activation, the practitioner might train the location at "C3" which was producing 20 femto Teslas to reward or encourage the location to produce 30 femto Teslas. Therefore, the color blue which could be understood as a "cold" color could represent the amount of energy (20 femto Teslas) produced at that site and the patient could be incrementally rewarded with color spectrum increasing to red representing 30 femto Teslas (i.e., blue, green, yellow, orange, red), thus training the brain to increase the energy at that location.

The following U.S. patents are all incorporated by reference in this disclosure:

| | | | | |
|---|---|---|---|---|
| 6,275,719 | 6,269,262 | 6,195,576 | 5,211,178 | 5,020,538 |
| 5,709,645 | 5,024,235 | 5,899,867 | 5,241,967 | 5,571,057 |
| 4,919,143 | 5,409,445 | 4,949,726 | 5,365,939 | 5,877,447 |
| 6,291,759 | 4,263,561 | 5,230,344 | 4,320,768 | 4,474,186 |
| 4,747,082 | 4,928,704 | 4,955,388 | 5,010,891 | 5,123,899 |
| 5,135,468 | 5,295,491 | 5,213,562 | 5,220,921 | 5,224,864 |
| 5,267,942 | 5,289,438 | 5,306,228 | 5,320,109 | 5,325,872 |
| 5,331,969 | 5,352,181 | 5,356,368 | 5,363,858 | 5,374,193 |
| 5,377,258 | 5,406,957 | 5,447,166 | 5,450,855 | 5,458,117 |
| 5,465,729 | 5,467,777 | | | |

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A neurofeedback system, comprising:
    an amplifier that receives EEG signals from a person;
    a color processor coupled to said amplifier; and
    a display unit coupled to said color processor;
    wherein said color processor dynamically converts an EEG signal from said amplifier to a color and shows the color on said display unit to a person being monitored;
    wherein said display unit comprises first and second displays that are independently controlled by said color processor; and
    wherein a predetermined color is provided on the first display simultaneously with the second display being provided with a color that is determined by said color processor based on the person's EEG.

2. The system of claim 1 wherein the second display is provided with a color that is based on an aspect of the person's EEG, the aspect selected from a group consisting of frequency and amplitude.

3. The system of claim 1 wherein the first and second displays are provided on head worn goggles.

4. The system of claim 1 wherein the display is located in a separate room from the person and is viewable by the person.

5. A method comprising:
    determining an aspect of a person's EEG;
    showing a target color on a first display viewable by the person; and
    showing a second color based on the aspect on a second display also viewable by the person simultaneously with the target color on the first display.

6. The method of claim 5 further comprising determining the aspect of the person's EEG as a frequency or an amplitude.

7. The method of claim 5 wherein showing the target and second colors comprise showing the target and second colors on first and second displays in a room apart from a room in which the person is located.

8. The method of claim 5 wherein showing target and second colors comprises showing the target and second colors on first and second displays provided in head worn goggles.

9. A system comprising:
    means for receiving a person's EEG signals;
    means for displaying a predetermined target color on a first display; and
    means for displaying a second color on a second display simultaneously with the target color, said second color being determined based on the person's EEG.

10. The system of claim 9 further comprising means for displaying the target and second colors in a room separate from the person.

11. The system of claim 9 further comprising means for determining the second color based on an aspect of the person's EEG, the aspect comprising frequency or amplitude.

* * * * *